(12) United States Patent
Smith (10) Patent No.: US 7,619,127 B2
(45) Date of Patent: Nov. 17, 2009

(54) METHOD OF OPERATING A RISER REACTOR

(75) Inventor: Jeffrey S. Smith, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 477 days.

(21) Appl. No.: 10/745,771

(22) Filed: Dec. 23, 2003

(65) Prior Publication Data

US 2005/0137439 A1 Jun. 23, 2005

(51) Int. Cl.
*C07C 1/00* (2006.01)
*B01J 8/18* (2006.01)
*F27B 15/08* (2006.01)
(52) U.S. Cl. ............... 585/640; 585/639; 585/921; 585/924; 422/139; 422/144; 422/145
(58) Field of Classification Search ......... 585/638–640, 585/921, 924; 422/144, 145, 139
See application file for complete search history.

(56) References Cited

U.S. PATENT DOCUMENTS

| | | | | |
|---|---|---|---|---|
| 4,379,123 | A * | 4/1983 | Daviduk et al. | 422/142 |
| 6,023,005 | A * | 2/2000 | Lattner et al. | 585/639 |
| 6,137,022 | A | 10/2000 | Kuechler et al. | 585/638 |
| 6,166,282 | A | 12/2000 | Miller | 585/638 |
| 6,613,290 | B1 * | 9/2003 | Senior | 422/140 |
| 2003/0009069 | A1 | 1/2003 | Vaughn et al. | 585/324 |

FOREIGN PATENT DOCUMENTS

WO  WO 01/62689 A1 * 8/2001
WO  WO 02/05941      * 1/2002

* cited by examiner

*Primary Examiner*—In Suk Bullock
(74) *Attorney, Agent, or Firm*—David M. Weisberg; Kevin M. Faulkner; Jaimes Sher (57) ABSTRACT

A method for maximizing the contact between solid catalyst particles and a feedstock while minimizing undesirable side reactions is provided. A plurality of feedstock jets are contacted with solid catalyst particles in a reactor having a non-homogenous contact zone and a unified flow contact zone.

29 Claims, 3 Drawing Sheets

METHOD OF OPERATING A RISER REACTOR

FIELD OF THE INVENTION

This invention relates to methods for controlling reactivity in a gas-solids reactor. Specifically, this invention relates to methods for optimizing the yield of oxygenate to olefin reactions.

BACKGROUND OF THE INVENTION

In industrial scale reactions for hydrocarbon to olefin conversion, the desired products are typically lighter olefins such as ethylene and propylene. During these industrial processes, it is also desirable to achieve nearly complete conversion of the oxygenate feedstock to olefins. Many of the factors, however, that enhance the overall conversion rate of the reaction also reduce the selectivity of the reaction for production of lighter olefins, and vice versa.

U.S. Pat. No. 6,166,282 B1 discloses a process for converting oxygenates to olefins in a reactor with two reaction zones. Feedstock is introduced into a lower, dense phase zone from a single inlet to effect a partial conversion to light olefins. The dense phase zone includes a fluidized catalyst bed. It is disclosed that as the feedstock continues to move up in the reactor, it moves into a transition zone above the dense phase zone where the reaction continues essentially to completion. The dense phase zone operates at a superficial velocity of less than 1 meter per second, and the transition zone operates at a superficial velocity of from 1 to 4 meters per second.

What is needed are additional methods to improve the effectiveness of oxygenate to olefin reactors as well as other fluidized bed reactors. In particular, methods are needed to allow for introduction of feedstock through the sidewalls of a reactor. Such systems are particularly desirable in maintaining high selectivity to ethylene and propylene products while maximizing reactivity during oxygenate to olefin reactions.

SUMMARY OF THE INVENTION

This invention generally provides processes for converting oxygenate feedstock to olefin products. In an embodiment, the process begins by a) contacting an olefin forming catalyst flowing through a contacting conduit with individual jets of oxygenate at an angle inclined from the flow of the olefin forming catalyst to initiate conversion of the oxygenate to olefin product. The individual jets are then mixed together downstream within the reactor at a location in the contacting conduit. This mixed flow continues through the reactor to a connecting conduit having a cross sectional area less than that of the contacting conduit to continue conversion of the oxygenate to olefin product.

In another embodiment, the process begins by contacting an olefin forming catalyst that is flowing through a contacting conduit with individual jets of oxygenate at an angle inclined from the flow of the olefin forming catalyst. The olefin forming catalyst and oxygenate then flow into a unified flow contact zone within the contacting conduit. The olefin forming catalyst and oxygenate continue to flow from the unified flow contact zone through a connecting conduit having a cross sectional area less than that of the expanded conduit.

In still another embodiment, the process starts by flowing an olefin forming catalyst through an initial conduit. The olefin forming catalyst flows from the initial conduit through an expanded conduit having a non-homogeneous contact zone and a unified flow contact zone. The olefin forming catalyst is contacted with oxygenate in the non-homogeneous contact zone. The olefin forming catalyst and oxygenate then flow from the non-homogeneous contact zone to the unified flow contact zone. This flow continues from the expanded conduit to an extended conduit having a cross sectional area less than that of the expanded conduit.

In yet another embodiment, the process of converting an oxygenate to an olefin begins by flowing an olefin forming catalyst from an initial conduit through a contacting conduit having an expanded cross sectional area. The olefin forming catalyst flowing through the contacting conduit is contacted with individual jets of oxygenate at an angle inclined from the flow of the olefin forming catalyst to initiate conversion of the oxygenate to olefin product. These individual jets are mixed together downstream of contact at a location within the contacting conduit. The downstream mixture the flows to a connecting conduit having a cross sectional area less than that of the contacting conduit to continue conversion of the oxygenate to olefin product.

Desirably, the processes of the above embodiments may be expanded to comprise a method for making a polyolefin. The above processes can be extended by separating olefin product formed during flow through the reactor from the olefin forming catalyst. At least one olefin from this separated olefin product is then contacted with an olefin forming catalyst to form polyolefin.

DETAILED DESCRIPTION OF THE EMBODIMENTS

I. Maximizing Contact and Minimizing Side Reactions

This invention provides a method for maximizing contact between a feedstock stream and a flow of catalyst particles, while minimizing undesirable side reactions. In particular, this invention maximizes contact between oxygenate compounds and catalyst particles that convert the oxygenate to olefin products having substantial quantities of ethylene and propylene.

In an embodiment, olefin forming catalyst particles in a reactor are passed through an initial conduit and into a contacting conduit. Preferably, the contacting conduit has a greater cross-sectional area than the initial conduit.

In another embodiment, the flow of catalyst particles into the contacting conduit are in the form of a fluidized bed of particles. As the catalyst particles flow through the contacting conduit, one or more flows of oxygenate feedstock are introduced through the sidewall of the contacting conduit. Desirably, the oxygenate feedstock is injected as a plurality of jets that are at an angle relative to the direction of flow within the contacting conduit. As the feedstock jets pass through the fluidized bed, the oxygenate feedstock contacts the catalyst particles and entrains some of the catalyst particles in the jets. This contact between the catalyst particles and the feedstock jets begins the conversion process.

The feedstock jets will move through the fluidized bed of catalyst particles until the jets contact or interfere with each other. At this point, the fluidized bed ends and the character of the flow structure begins a transition from individual jets within a bed of catalyst particles to a unified, plug-flow type flow structure of gas with entrained solids. This transition occurs either without creation of an intermediate turbulent zone between the individual jet flow region and the unified flow region, or with creation of only a small turbulent zone. The transition from jet characteristics to plug-flow characteristics with only a minimal turbulent zone results in a maximum amount of reactive contact between the feedstock and the solid catalyst particles. This produces increased conversion of feedstock for a given length of flow of catalyst and feed through the reactor system, while keeping undesirable side reactions to a minimum.

The transition from individual feedstock jets with entrained particles to a single, unified gas-solids flow takes place within the contacting conduit. This transition can be viewed as dividing the contacting conduit into two regions. The first region in the contacting conduit is a non-homogenous contact zone. This is the portion of the conduit where the jets of oxygenate feedstock retain their individual character. The flow in this region is characterized by distinct jets of oxygenate feedstock passing through a fluidized bed of particles. The concentration of particles within the feedstock jets is lower than the concentration of particles in the surrounding fluidized bed. This concentration difference results in the non-homogenous character of the region, as there are distinct areas of higher and lower catalyst particle concentration.

The feedstock jets initially enter the contacting conduit at an angle relative to the direction of flow within the contacting conduit. As the jets move through the fluidized bed, the jets will move toward each other. The jets will also expand as they move downstream through the fluidized bed. As a result, the jets will eventually converge and form a single flow. In the region of the contacting conduit upstream from the convergence of the jets, the flow structure of the jets can be described as individual feedstock jets separated by interstitial space. The interstitial space refers to the space separating the individual oxygenate jets. In the contacting conduit, this interstitial space is occupied by the fluidized bed of catalyst particles. The second region in the contacting conduit is a unified flow contact zone. In this region, the oxygenate feedstock jets have lost their individual character, leaving a single flow of feedstock and particles.

The flow of feedstock and particles than passes into the connecting conduit. Preferably, the connecting conduit has a smaller cross-sectional area than the contacting conduit. In one embodiment, less than 100% of the oxygenate feedstock passing through the contacting conduit is converted into olefins. Similarly, in an embodiment, less than 100% of the oxygenate feedstock passing through the connecting conduit is converted into olefins.

After conversion, the olefins can be separated from the flow and used in another process, such as the formation of polyolefins. After separating out at least one of the converted olefins, the converted olefin can be contacted with another catalyst to form a desired polyolefin.

The discussion that follows will refer to flows of feedstock and catalyst particles. It is understood that once a flow of oxygenate feedstock comes into contact with catalyst particles, the conversion reaction from oxygenate to olefin will begin. Thus, as the flow of oxygenate feedstock and catalyst moves downstream, the flow will contain an increasing amount of olefin. Those of skill in the art will recognize that once the oxygenate feedstock is brought into contact with the olefin forming catalyst particles, the flow within the reactor will be a combination of oxygenate feedstock, olefin formed from conversion of feedstock, and catalyst particles.

II. Flow Conditions

A. The Initial Conduit

The flow within the reactor begins with the introduction of solid catalyst particles, such as olefin forming catalyst particles, into the initial conduit. The catalyst particles entering the initial conduit can be newly added particles, particles returning from a regenerator, or particles that have bypassed a regenerator. In preferred embodiments, the catalyst particles enter the initial conduit along with a gas stream in order to set up a fluidized bed within the reactor.

B. The Contacting Conduit

After the catalyst particles flow through the initial conduit, the catalyst particles enter the contacting conduit. In an embodiment, the contacting conduit will have a larger cross-sectional area than the initial conduit. For example, at the location where the initial conduit and contacting conduit are joined, the walls of the contacting conduit can be angled outward to increase the cross-sectional area of the contacting conduit.

In the contacting conduit, the catalyst particles are contacted with one or more flows of oxygenate feedstock. In an embodiment, the oxygenate feedstock is introduced into the contacting conduit as a plurality of jets. These jets can be introduced at any elevation within the contacting conduit. Because the jets are entering through the sidewall of the reactor, the feedstock inlets will be oriented at an angle relative to vertical. Typical angles of entry for the feedstock inlets are between 15° and 75° from vertical, with the inlets oriented so that the feedstock jets are aligned with the direction of flow in the reactor. In an embodiment, the feedstock jets enter the contacting conduit through the angled portion of the sidewalls.

When the feedstock jets enter the contacting conduit, the combination of the jets and catalyst particles form a non-homogenous contact zone. Initially, the feedstock jets will retain their individual character as the jets pass through the bed of solid catalyst particles. The flow structure within the non-homogenous contact zone consists of feedstock jets that contain no catalyst particles surrounded by a fluidized bed of catalyst particles. The initial size of the feedstock jets is dictated by the size of the nozzles used to inject the feedstock into the contacting conduit. Once the jets enter the contacting conduit, however, the jets will expand and start to capture particles from the surrounding fluidized bed. As long as the feedstock jets retain their individual character, the interstitial space between the jets is occupied by solid catalyst particles from the fluidized bed. Thus, as the jets move downstream through the reactor and continue to expand, more and more catalyst particles are captured, or entrained, in the feedstock flows. This leads to increasing catalyst particle concentration within the feedstock jets, and thus increasing contact between the catalyst particles and the feedstock.

Because the feedstock jets are expanding and are injected at an angle relative to vertical, the individual jets will eventually converge and coalesce into a single flow. The elevation within the reactor where the jets coalesce defines a transition between the non-homogenous contact zone and a unified flow contact zone. Preferably, this transition takes place within the contacting conduit. After entering the unified flow contact zone, the flow of feedstock and catalyst particles continues downstream in the reactor toward the connecting conduit.

C. The Connecting Conduit

After passing through the contacting conduit, the flow of feedstock and solid catalyst particles enters the connecting conduit. In an embodiment, the connecting conduit will have a smaller cross-sectional area than the contacting conduit. This will increase the speed of the feedstock and catalyst particle flow as it passes through the connecting conduit. The change in cross-sectional area can be achieved by angling the walls of the connecting conduit inward.

The flow within the connecting conduit continues the flow formed in the unified flow contact zone. In preferred embodiments, the flow in the connecting conduit will form an annular, plug-like flow structure. In this annular flow structure, the solid catalyst particles are concentrated near the wall of the reactor, leaving a central core with a reduced particle concentration. The plug-flow like region has the lowest reaction rate of the three regions due in part to a lower solid catalyst particle concentration. However, this lower concentration also leads to improved reaction selectivity, leading to increased production of ethylene and propylene versus other olefins. The plug-flow like characteristics of the final reaction zone are desirable in order to achieve a balance between converting as much oxygenate to olefin as possible while still maintaining high selectivity for production of ethylene and propylene.

The connecting conduit is the final reaction area the feedstock and catalyst particle flow passes through. After passing through the connecting conduit, the catalyst particles are removed from the flow to stop the conversion reaction. The olefins formed by the conversion reaction are also separated from the flow.

D. Process Conditions within the Conduits

The reaction rate and reaction products for the oxygenate to olefin reaction depend on several factors, such as the level of coke on the catalyst particles and the reaction temperature. The reaction rate and reaction products are also influenced by the concentration of catalyst particles the feedstock is exposed to. For example, exposing an oxygenate feedstock to higher densities of catalyst particles results in faster conversion of oxygenate to olefins. However, higher catalyst particle densities also tend to lead to production of higher molecular weight olefins rather than ethylene and propylene. By contrast, exposing feedstock to lower catalyst particle densities results in lower reaction rates but higher selectivity for production of ethylene and propylene.

One way to achieve a balance between higher reaction rates and higher selectivity is to perform the reaction in an environment that can support multiple reaction conditions. For example, the reaction can be carried out in a gas-solids reactor with a fluidized bed of catalyst particles. In this example, oxygenate feedstock is passed through the bed of catalyst particles. This exposes the oxygenate to a relatively high concentration of catalyst particles, leading to a faster reaction rate. As the feedstock passes through the bed of particles, some of the particles are carried with the gas out of the fluidized bed. After the feedstock leaves the bed of catalyst particles, some of the catalyst particles stay entrained in the gas flow to allow the reaction to continue, although at a lower rate due to the lower concentration of particles.

In this invention, the process conditions within the reactor change several times as the olefin forming catalyst particles and oxygenate feedstock move downstream through the reactor. Beginning with the initial conduit, the catalyst particles move through the conduit at a velocity of from about 0.1 ft/s to about 3 ft/s, preferably from about 0.5 ft/s to about 1.5 ft/s. The solid volume fraction of the catalyst particles in the initial conduit is from about 20% to about 40%, preferably from about 30% to about 35%. In the initial conduit, the velocity and concentration of the catalyst particles are controlled in part by the velocity of the fluidizing gas used to set up the fluidized bed.

The velocity and concentration of the catalyst particles remain relatively constant until the catalyst particles are contacted with the flows of feedstock in the contacting conduit. In an embodiment, the velocity of an oxygenate feedstock flow as it enters the contacting conduit is from about 75 ft/s to about 125 ft/s, preferably from about 90 ft/s to about 110 ft/s.

When the feedstock jets come into contact with the bed of catalyst particles, the jets begin to slow down, expand, and entrain solid particles within the jet flow. This process continues throughout the non-homogenous contact zone. By the time a feedstock flow reaches the top of the non-homogenous contact zone, the velocity of the feedstock flow typically drops to from about 18 ft/s to about 30 ft/s. During this time, the concentration of solid particles entrained in the flow increases, having up to 15% by volume of solid particles in the flow. This concentration, however, desirably remains below the concentration of the fluidized bed of solid particles in the surrounding interstitial space. In an embodiment, the concentration of solid particles within the feedstock jets is from about 1% by volume to about 15% by volume. The concentration of the solid particles in the interstitial space preferably remains within about 5% of the fluidized bed values, preferably from about 20% to about 40% by volume, and most preferably from about 30% to about 35% by volume.

Note that the feedstock jets entering the contacting conduit can serve as additional fluidization gas. Desirably, the introduction of feedstock increases the height of the fluidized bed.

When the feedstock flows and catalyst particles reach the end of the non-homogenous contact zone, the feedstock flows desirably converge to form a unified flow contact zone having a single flow. This transition roughly corresponds to the top of the fluidized bed of particles. As noted above, the unified flow contact zone may begin with a turbulent reaction area. The turbulent reaction area is a region where the oxygenate jets have converged, but no other ordered flow structure has developed. This turbulent region is sometimes referred to as an engulfing zone. Flow structures that lead to smaller engulfing zones typically also lead to increased contact between the feedstock and catalyst particles while minimizing undesirable side reactions. In an embodiment, the height of an engulfing zone within the reactor is not greater than 2 feet, and is preferably not greater than 0.5 feet.

In the unified flow contact zone, the velocity of the single flow is preferably from about 18 ft/s to about 30 ft/s. It is also preferred that the concentration of solid catalyst particles in the unified flow reaction zone is less than the concentration of catalyst particles in the non-homogenous contact zone. At the downstream end of the unified flow reaction zone, where the feedstock and catalyst particle flow enters the connecting conduit, the concentration of solid catalyst particles within the flow is desirably from about 1% to about 3% by volume.

When the flow of feedstock and catalyst particles (as well as any olefins created by conversion of the feedstock) enters the connecting conduit, there is preferably an increase in the flow velocity. In preferred embodiments, the flow is in a plug-flow like flow pattern within the connecting conduit. At this point, the gas superficial velocity (GSV) is sufficient to provide plug-flow characteristics. The GSV is a measure of the average velocity for gases moving through the reactor. Desirably, the GSV for the flow in the connecting conduit is at least be 9 m/s. In an embodiment, the GSV for the flow in the final reaction zone is from about 9 m/s to about 25 m/s, preferably from about 12 m/s to about 20 m/s.

III Types of Reactor Systems

A. Oxygenate to Olefin Reactors

The method of this invention can be adapted for use in a variety of catalytic reactors such as fluidized bed reactors, fast fluidized bed reactors, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor types are riser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282 (fast-fluidized bed reactor), and U.S. Pat. No. 7,102,050 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction region within one or more riser reactor(s) and a second reaction region within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 99.9 weight percent, such as from about 1 weight percent to about 99 weight percent, more typically from about 5 weight percent to about 95 weight percent based on the total weight of the feedstock including any diluent contained therein. The liquid and vapor feedstocks may be the same composition, or may contain varying proportions of the same or different feedstocks with the same or different diluents.

The process of this invention can be conducted over a wide range of temperatures, such as in the range of from about 200° C. to about 1000° C., for example from about 250° C. to about 800° C., including from about 250° C. to about 750° C., conveniently from about 300° C. to about 650° C., typically from about 350° C. to about 600° C. and particularly from about 350° C. to about 550° C.

Similarly, the process of this invention can be conducted over a wide range of pressures including autogenous pressure. Typically the partial pressure of the feedstock exclusive of any diluent therein employed in the process is in the range of from about 0.1 kpaa to about 5 MPaa, such as from about 5 kPaa to about 1 MPaa, and conveniently from about 20 kpaa to about 500 kpaa.

The solids particles and gas are flowed through the gas-solids reactor at a solids to gas mass ratio of about 5:1 to about 75:1. Preferably, the solids particles and gas are flowed through the gas-solids reactor at a solids to gas mass ratio of about 8:1 to about 50:1, more preferably from about 10:1 to about 40:1.

During the conversion of a hydrocarbon feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

The feedstock entering the reactor system is preferably converted, partially or fully, in the first reactor region into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450°° C. to about 750° C., and conveniently from about 550° C. to 700° C. The regeneration pressure may be in the range of from about 15 psia (103 kpaa) to about 500 psia (3448 kpaa), such as from about 20 psia (138 kPaa) to about 250 psia (1724 kpaa), including from about 25 psia (172 kPaa) to about 150 psia (1034 kPaa), and conveniently from about 30 psia (207 kPaa) to about 60 psia (414 kpaa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, 1997 (336-337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene ($C2$) splitter, propylene ($C3$) splitter and butene ($C4$) splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in Kirk-Othmer Encyclopedia of Chemical Technology, 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. Pat. No. 6,593,506 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4$+hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4$+impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

B. Description of Solid Particles

The solids that flow through the gas-solids reactor system of this invention are compounds that are solid at the conventional operating conditions of the reactor. The solids can be inert materials, catalytic materials, or a mixture thereof. Preferably, the solids are catalyst particles.

In one embodiment, the catalyst particles which are flowed through the gas-solids reactor system of this invention are molecular sieve catalysts, such as a conventional molecular sieve. Examples include zeolite as well as non-zeolite molecular sieves, and are of the large, medium or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1-67, Elsevier Science, B. V., Amsterdam, Netherlands (2001).

The small, medium and large pore molecular sieves have from a 4-ring to a 12-ring or greater framework-type. In a preferred embodiment, the molecular sieves have 8-, 10- or 12- ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [$TO_4$] tetrahedral units, more preferably, two or more [$SiO_4$], [$AlO_4$] and/or [$PO_4$] tetrahedral units, and most preferably [$SiO_4$], [$AlO_4$] and [$PO_4$] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZNAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [$QO_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, $SAPO_4$ (UIO-6)), U.S. Pat. No. 6,004,898 (molecular sieve and an alkaline earth metal), U.S. Pat. No. 6,743,747 (integrated hydrocarbon co-catalyst), PCT WO 01/64340 published Sep. 7, 2001 (thorium containing molecular sieve), and R. Szostak, Handbook of Molecular Sieves, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. Pat. No. 6,812,372 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

In one embodiment, the molecular sieves used in the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a D90 particle size distribution of less than about 1 µm.

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

The catalyst particles used according to this invention can also be maleic anhydride forming catalysts. In one embodiment, the maleic anhydride forming catalyst comprise a mixed oxide containing vanadium and phosphorus as major constituent elements (vanadium-phosphorus mixed oxide). Examples of such catalysts include those comprising divanadyl pyrophosphate ($(VO)_2 P_2O_7$) as the active component. Details of these catalysts including production processes are disclosed, for example, in Chem. Rev., 88, pp. 55-80 (1988), JP-B-4-24104, and U.S. Pat. Nos. 4,472,527 and 4,520,127, the descriptions of which are incorporated herein by reference.

Inert solid particles can be flowed through the reactor system of this invention. The inert solid particles can be mixed with solid catalyst particles or used as carrier materials for any conventional catalyst. Examples of such inert solid materials include oxides, such as silica, alumina, titania and zirconia. Of these oxides, silica is preferred. Silica is inherently inert, differing from other solid materials, and can serve as an excellent binder for the ingredients of the oxide catalyst composition without impairing the selectivity of many catalyst compositions. Such material also serves to impart the resulting catalyst composition with a high attrition resistance. When used as carrier, the silica can be in the range of about 30% to about 70% by weight, preferably about 40% to about 60% by weight, based on the total weight of the catalyst composition and the carrier.

C. Types of Feedstock

In one embodiment, the chemical reactant is an oxygenate and the catalyst particles are molecular sieves. Molecular sieves capable of converting the oxygenate to olefins are preferred. Any of the above described molecular sieves can be used. Conventional zeolites and silicoaluminophosphates are preferred.

Oxygenates used in this invention include one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In another embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

In still another embodiment, the products from a conversion reaction can be used as raw materials for a subsequent process. For example, many of the olefins produced by an oxygenate to olefin conversion reaction are suitable for use as raw materials for the synthesis of polyolefins, such as polyethylene or polypropylene.

IV. Examples

A. Sample Apparatus

Figure 1:
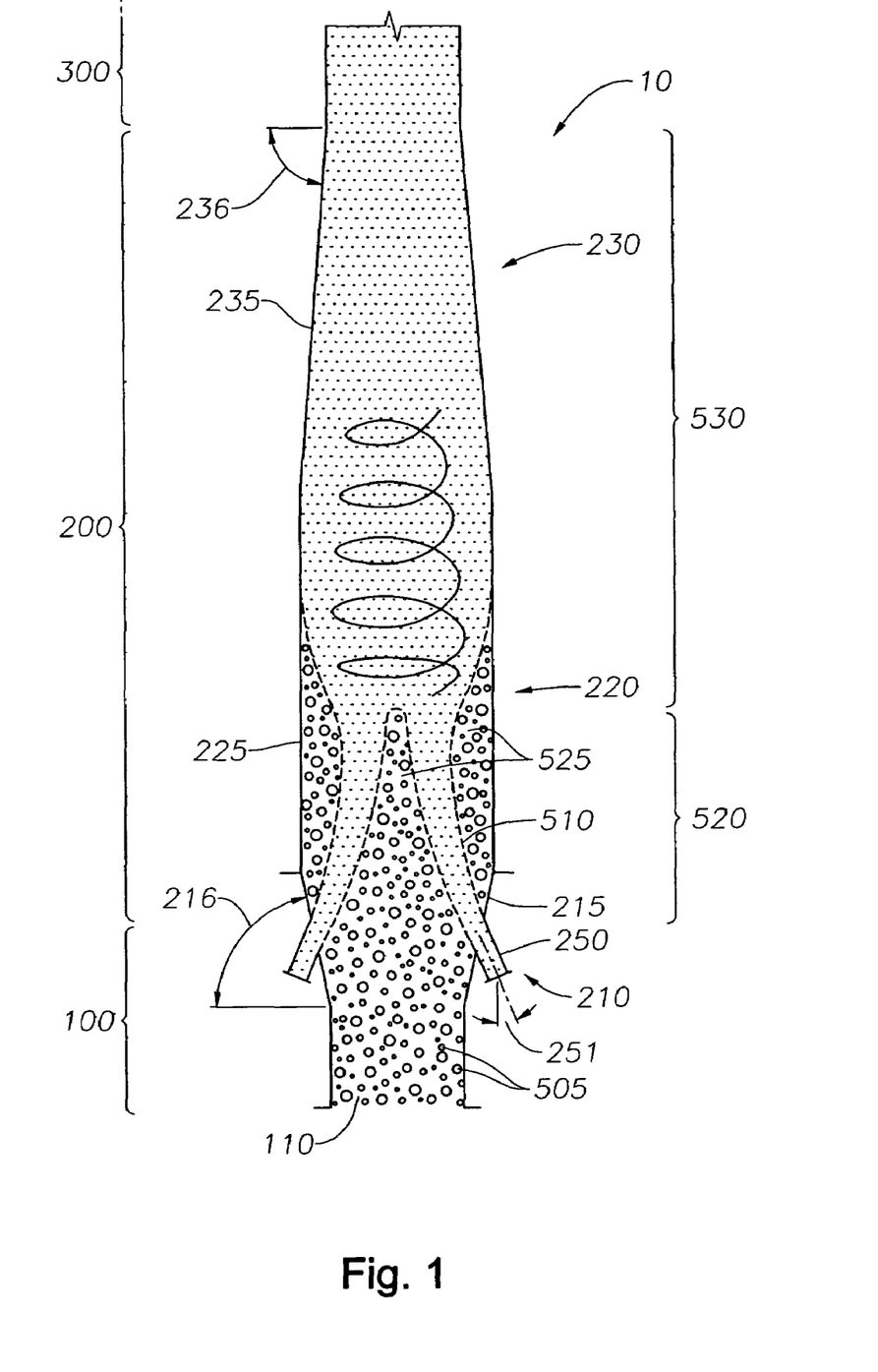
FIG. 1 schematically shows the lower portion of a reactor suitable for use in carrying out the present invention.

FIG. 1 provides an example of a lower portion 10 of a reactor suitable for performing the method of this invention. The lower portion 10 of the reactor shown in FIG. 1 would typically be part of a larger riser reactor, such as the reactor systems described above. Lower portion 10 is composed of an initial conduit 100, a contacting conduit 200, and a connecting conduit 300. Catalyst enters initial conduit 100 of the reactor through catalyst inlet 110. In an embodiment, the catalyst entering initial conduit 100 is returned from a recirculation loop that includes a regenerator as described above for at least partially regenerating the solid catalyst particles. Initial conduit 100 is openly joined to contacting conduit 200. Contacting conduit 200 is composed of a bottom frustum 210, a barrel 220, and an upper frustum 230. In an embodiment, sidewall 215 of bottom frustum 210 is angled so that the diameter of the frustum increases in the direction away from catalyst inlet 110. In an embodiment, sidewall 215 forms an angle 216 of 75 degrees relative to grade.

Feedstock inlets 250 are openly joined to contacting conduit 200 through sidewall 215. Feedstock inlets 250 form a non-zero angle relative to vertical as they enter bottom frustum 210. Feedstock inlets 250 join bottom frustum 210 at an angle 251. In an embodiment, angle 251 has a value of 30 degrees relative to vertical.

Within contacting conduit 200, bottom frustum 210 is openly joined to barrel 220. The connection between bottom frustum 210 and barrel 220 is shown as a flange joint. The connection between bottom frustum 210 and initial conduit 100 is also shown as a flange joint. The flange joints allow the bottom frustum to be disconnected more easily so that different nozzle configurations can be attached to the reactor. Barrel 220 should be tall enough to at least contain the full height of the non-homogenous reaction zone and the transition to the uniform flow reaction zone during operation. Sidewall 225 is a vertical sidewall.

Barrel 220 is openly joined to upper frustum 230. Upper frustum 230 narrows the width of the reactor back to the final desired dimension for riser (connecting conduit) 300. In an embodiment, sidewall 235 of upper frustum 230 forms an angle 236 of 85 degrees. In an embodiment of this invention, the region from bottom frustum 210 to upper frustum 230 corresponds to a contacting conduit. The catalyst, reacted feedstock, and unreacted feedstock continue up connecting conduit 300 until they reach a separator.

In the embodiment depicted in FIG. 1, the diameter of initial conduit 100 is 5 feet. The diameter of barrel 220 is 8.5 feet, while the diameter of connecting conduit 300 is only 6 feet. The change in width between these sections aids in the development of the desired flow regimes. Within barrel 220, the increased diameter allows the feedstock jets to spend more time travelling through the fluidized bed in the non-homogenous reaction zone prior to coalescing with each other. This increases the possible height of the fluidized bed, and thus increases the amount of time the feedstock spends in the non-homogenous reaction zone. After leaving barrel 220, the reduction in the size of the riser to 6 feet results in an increased GSV for the feedstock flow. This helps the feedstock flow achieve the desired GSV of greater than 9 m/s.

During an oxygenate to olefin conversion process, solid catalyst particles 505 will enter reactor 10 through initial conduit 100. As the particles move up through the reactor and into contacting conduit 200, the particles 505 will come into contact with oxygenate feedstock jets 510. Within the contacting conduit, this will lead to formation of at least two flow areas. Near the entry point of the feedstock jets 510, a flow structure will develop that is composed of the jets 510 and interstitial areas 525 between the jets. This area is indicated as contacting zone 520. As the flow moves downstream, the jets will eventually coalesce to form a single flow in mixing zone 530. The mixed flow then continues downstream into connecting conduit 300.

B. Characterizing Reactor Flows—Simulation Methodology

To further investigate the flow structure of hydrocarbon to olefin reactions within a gas-solids reactor, a jet-mixing model to describe a flow of methanol (oxygenate) from a plurality of feed nozzles into a reactor was developed. This jet-mixing model was used to model a reactor having a lower portion as shown in FIG. 1. In the model, methanol feedstock enters the bottom frustum at the circumference. In the model, the feedstock inlet nozzles are located in a plane parallel to grade and below upper frustum 235. The nozzles are equally spaced along the circumference. The nozzles are angled from the vertical by an angle theta, where theta must be located at an elevation below the nozzle plane. A jet of methanol exits each nozzle at about 96 ft/s. The jet is initially small in diameter and grows steadily as the jet decelerates. Surrounding the jet is a dense phase comprised of aeration fluid and solids. Owing to the concentration difference between the jet and the dense phase, solids become entrained into the jet. The percentage of solids entrained in the jet flow is referred to as the solids holdup. The volume fraction of solids increases as the jet penetrates the riser. Eventually all of the jets coalesce and engulf the entire cross section of the riser. Immediately above the engulfing zone, the classical core-annuluar flow structure develops in the riser. The important physical quantities needed to describe reaction kinetics are the volumes of the jets, the solids holdup, and the volume of the engulfing zone. The following model equations were used to develop a jet mixing model to simulate the flow structure within a reactor. These equations show that the key jet mixing parameters are the jet entrainment coefficient, the angle of the nozzles relative to vertical, and nozzle velocity.

1. Jet Mixing Physics

The location of the jet center in the riser at any distance, l, along the length of the jet is $(Z_c, R_c)$. The position of the center of the jet changes according to $$\frac{dZ_c}{dl} = \frac{U_o \cos\theta}{U_l}$$

$$\frac{dR_c}{dl} = -\frac{U_o \sin\theta}{U_l}$$

where $U_0$ is the injection velocity and $U_1$ is the jet velocity. The rate of entrainment of solids into the jet is $$\psi = \alpha \left[\frac{\rho_j}{\rho_a}\right]^{0.5} U_l$$

where $\alpha$ is the entrainment coefficient and $r_j$ and $r_a$ are the jet and emulsion phase densities, respectively. The mass and momentum balances rounding out the description of the jet are $$\frac{d}{dl}[\pi R_j^2 U_l] = 2\pi R_j \psi$$

$$\frac{d}{dl}\phi = \frac{2\psi(\phi_s - \phi)}{R_j U_l}$$

$$\frac{d}{dl}[\pi R_j^2 \rho_j U_l U_r] = 0$$

$$\frac{d}{dl}[\pi R_j^2 \rho_j U_l U_z] = 2\pi R_j \rho_a \psi V_s + \pi R_j^2 g(\rho_a - \rho_j)$$

The engulfing zone height is estimated to be $$H_{engulf} = \frac{(R_{barrel} - R_{core})}{\alpha \left(\frac{\rho_{core}}{\rho_{emulsion}}\right)^{0.5} \left(\frac{U_{core}}{V_s}\right)}$$

where Rbarrel is the radius of the lower portion of the riser, Rcore is the equivalent diameter of the jets after coalescence, and Vs is the emulsion phase velocity. A mass balance determines the resulting solids holdup for the engulfing zone.

2. Frustum-Barrel Geometric Equations $$V_{frust} = \frac{\pi \tan\theta}{3}(R_{barrel}^3 - r_{riser}^3)$$

$$= \frac{\pi h_{frust}}{3}(R_{barrel}^2 + R_{barrel} R_{riser} + R_{riser}^2)$$

$$V_{barrel} = \pi R_{barrel}^2 H$$

$$V_{simulation} = V_{frust} + V_{barrel}$$

The angle, $\theta$, in this model is the angle from the horizontal that describes the tapering element (frustum angle) between the barrel and the riser.

Other important operating parameters include conversion, pressure, temperature, catalyst-to-oil ratio, and coke level which have values of 95%, 25 psig, 490 C, 30:1, and 5 wt %, respectively.

C. Characterizing Reactor Flows—Flow Structure Within the Non-Homogenous Contact Zone FIGS. 2-5 provide examples of the progress of feedstock jets through a fluidized bed. These examples were generated by simulating the introduction of feedstock jets into a reactor as depicted in FIG. 1. In the simulations, methanol feedstock was injected into an 8.5 foot diameter reactor through the sidewall of the reactor via 6 12" nozzles. The velocity of the feedstock as it exits the nozzles is 96 ft/sec. The emulsion velocity for the fluidized bed (prior to injection of the feedstock jets) was 2.26 feet/second.

Figure 2:
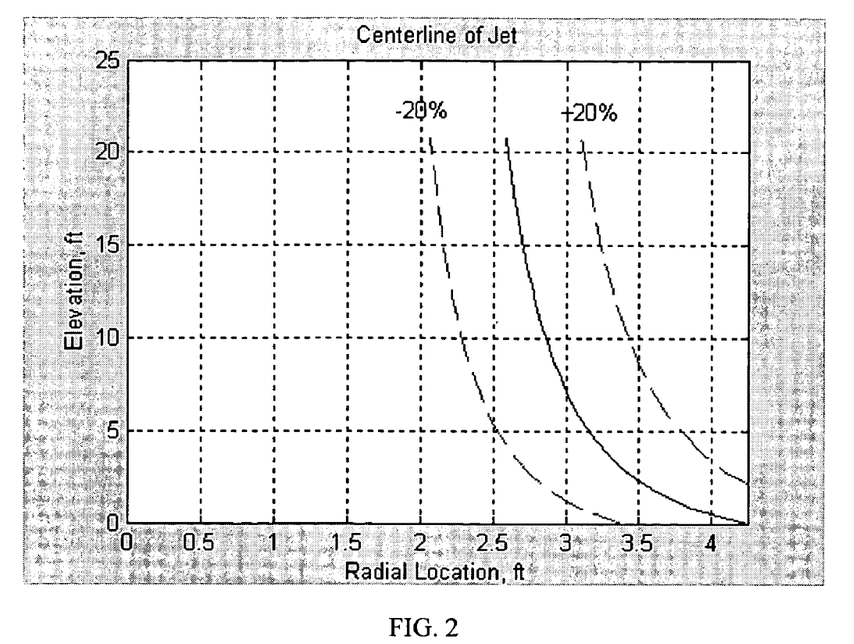
FIG. 2 depicts information regarding the flow structure in a reactor when performing a gas-solids reaction according to the present invention.

FIG. 2 depicts the motion of the centerline for each of the jets. The middle curve represents the simulated center of the jet, while the two dotted lines represent rough error bounds on the calculated trajectory. The centerline of the jet initially starts out at a height of zero within the reactor and at a distance of 4.25 feet from the center of the reactor (half the diameter). The figure shows the predicted progress of the centerline of the jet as it moves through the fluidized bed. The jet continues through the fluidized bed until it reaches a height of 21.9 feet, where the jets begin to interfere and the fluidized bed ends.

Figure 3:
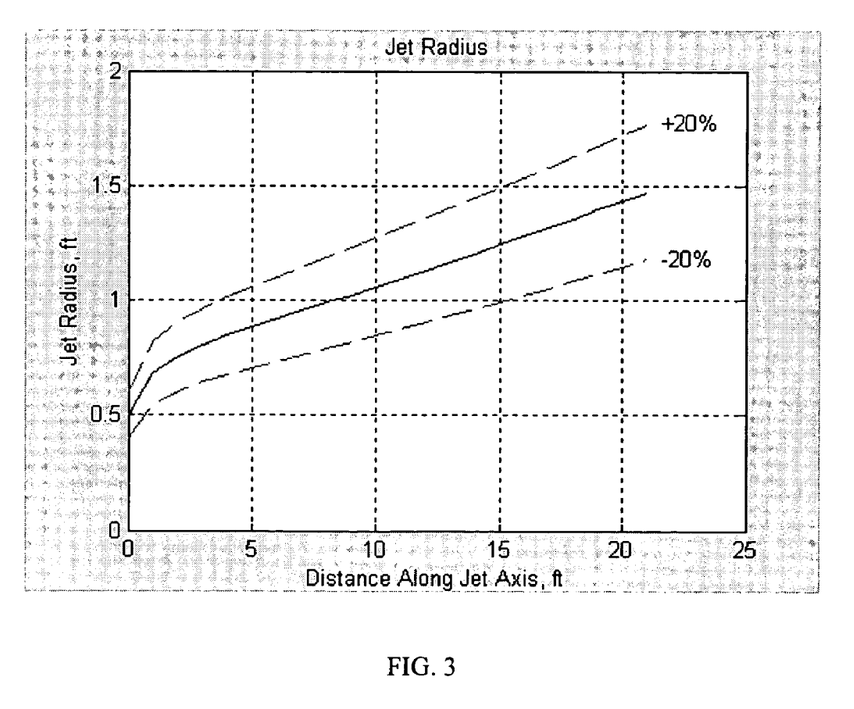
FIG. 3 depicts information regarding the flow structure in a reactor when performing a gas-solids reaction according to the present invention.

FIG. 3 shows the expansion of the jet as it moves through the fluidized bed. Here, the bottom axis represents the total distance the jet has traveled, rather than the height of the jet within the fluidized bed. The jet starts out with an initial radius of 0.5 feet. As the jet travels through the fluidized bed, the radius expands until the jet reaches its final radius of about 1.5 feet.

Figure 4:
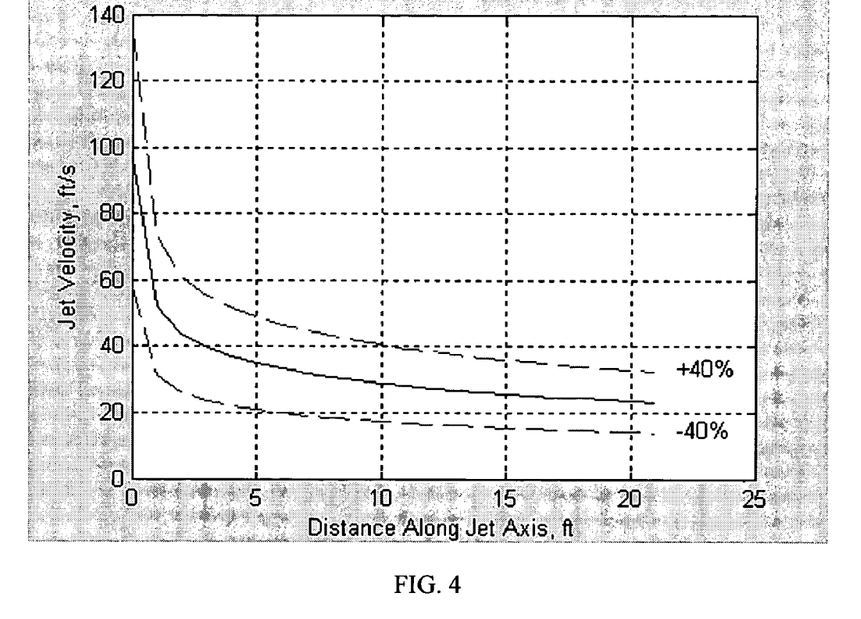
FIG. 4 depicts information regarding the flow structure in a reactor when performing a gas-solids reaction according to the present invention.

FIG. 4 shows the velocity of the feedstock jet as it travels through the fluidized bed. After an initial sharp drop off in velocity, the jet approaches a velocity of about 20 ft/sec.

Figure 5:
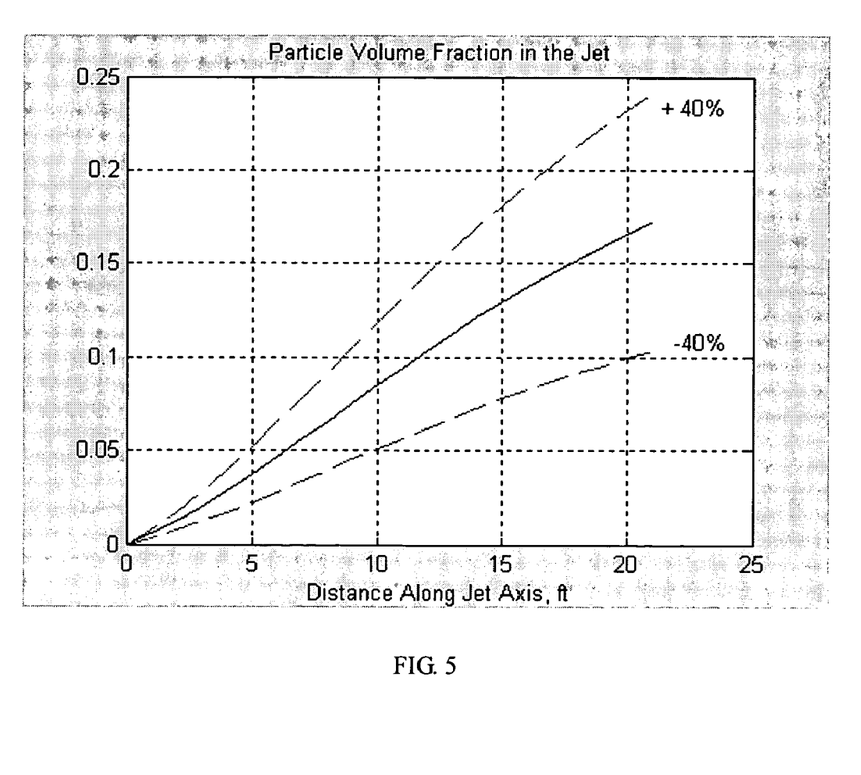
FIG. 5 depicts information regarding the flow structure in a reactor when performing a gas-solids reaction according to the present invention.

FIG. 5 shows the particle volume fraction of a feedstock jet as it travels through the fluidized bed. As the feedstock moves up through the bed, the jet accumulates solid particles. At the top of the bed, the feedstock contains a solid particle concentration of roughly 15% by volume.

These figures demonstrate the typical behavior for feedstock jets in the acceleration zone. As the jets move through the fluidized bed, the jets expand, slow down, and entrain solid catalyst particles. The exact values for the height of the fluidized bed and the size, speed, and particle volume of the jets will vary depending on the initial velocity of the jets and the angle of the nozzles relative to vertical. However, the qualitative appearance of the flow structure as a series of lower concentration jets within the higher concentration fluidized bed should remain the same.

D. Characterizing Reactor Flows—Gas-Solids Reactivity

To simulate reactivity within a gas-solids reactor, the jet mixing model was combined with 1D and 2D reactor kinetics modules. In these combined jet mixing and reaction kinetics simulations, the jet was first divided into finite cylindrical volume elements. The height of each cylindrical element was arbitrarily chosen as ~1 ft, and the diameter of each element was determined from the jet-mixing model. The number of finite elements, which ranged from 9 to 24, was in effect proportional to the axial penetration of the jet. The diameter of each volume element was then adjusted to account for the number of jets (or nozzles) present. Each element was then assigned the appropriate solid holdup corresponding to the location of the jet. Lastly, geometric criteria were selected to determine the onset of coalescence as well as the volume and solid fraction of the engulfing zone. During each computer simulation, the operating parameters for the base case remained constant; that is, the feed temperature, the catalyst-to-oil ratio, the upper zone hydrodynamics etc. were not adjusted. The initial parameters selected for the jet-mixing model are shown in Table 1. Simulations were conducted to explore the sensitivities to α (the entrainment coefficient), the angle of entry for the feedstock jets, and nozzle velocity. The response variables of interest were frustum conversion, acceleration zone height, holdup, and selectivity.

The value of the entrainment coefficient, α, is not easily determined for gas-solids flow. For single-phase flow, 0.08 has been reported in the literature. However, measurements for gas-solid flows indicate that entrainment is as much as a factor of two smaller.

Values calculated in these simulations are presented in Table 1. Mean jet holdup refers to the average concentration of solid particles entrained within a feedstock jet. As shown earlier in FIG. 5, the concentration of solid particles within a feedstock jet increases as the jet moves through the fluidized bed. The engulfing holdup similarly refers to the concentration of solid particles within the transition (engulfing) zone. The bottom zone conversion represents the percentage of feedstock converted to olefin in the accelerate (non-homogenous contact) zone and transition zone combined. To prevent overconversion of feedstock (and thus a loss of selectivity toward production of ethylene and propylene), the bottom zone conversion should be below about 90%.

Table 1 illustrates the sensitivity of the nozzle angle at a fixed α of 0.04. This value of the entrainment coefficient is believed to best represent the solids holdup behavior of the feedstock as it moves through the catalyst bed. The overall trend is that as the nozzles approach the horizontal, the height of the acceleration zone and the bottom zone conversion decrease. (The points shown for 15 degrees are lower than those at 30 degrees because the criteria for jet coalescence must change for steep angles to take into account the boundary provided by the riser wall. That is to say, the equivalent diameter obtained after combining the jets into one must not exceed the diameter of the riser.) At 75 degrees, the bottom zone conversion sharply increases owing to an increased engulfing zone height. Here, the engulfing zone contributes to the reaction more than the jets. In addition to showing a minimum in the size of the engulfing zone for an entry angle of 30 degrees from vertical, the simulations show that the maximum reactivity for the bottom zone in the reactor occurs at the largest fluidized bed height. The simulations also show that the largest fluidized bed size coincides with a minimization of the size of the engulfing zone.

Table 1 also includes a simulation involving a different nozzle configuration. The final column in Table 1 shows the results from a simulation with 12 8" jets oriented at an angle of 30 degrees. The feedstock from these jets was injected at a velocity of 129.4 ft/s. This inlet velocity was selected so that the total volume of feedstock entering the reactor was constant between the simulations involving 6 and 12 nozzles. Table 1 shows that although the engulfing zone height is relatively small (0.4 ft), the height of the fluidized bed is also small due to the higher feedstock jet velocity. This leads to a bottom zone conversion of only 0.3296. In spite of this lower bottom zone conversion value, this last case represents an embodiment of the present invention. The lower conversion value here merely indicates that for this nozzle configuration, the maximum bottom zone conversion is lower.

TABLE 1

|  | Jet Nozzle (in) | | | | | |
| --- | --- | --- | --- | --- | --- | --- |
|  | 12.00 | 12.00 | 12.00 | 12.00 | 12.00 | 8.00 |
| Num Jets | 6 | 6 | 6 | 6 | 6 | 12 |
| Angle of Jets | 15 | 30 | 45 | 60 | 75 | 30 |
| Jet Velocity (ft/s) | 96.5 | 96.5 | 96.5 | 96.5 | 96.5 | 129.4 |
| Entrainment alpha | 0.04 | 0.04 | 0.04 | 0.04 | 0.04 | 0.04 |
| Mean Jet Holdup | 0.0535 | 0.0565 | 0.0409 | 0.0286 | 0.0198 | 0.0468 |
| Ht engulfing zone (ft) | 0.0225 | 0 | 1.2087 | 0.7726 | 3.838 | 0.4028 |
| Engulfing holdup | 0.1145 | 0 | 0.1288 | 0.1456 | 0.1607 | 0.1 |
| Accel zone ht (ft) | 20.0 | 21.9 | 17.0 | 14.2 | 12.3 | 12.3 |
| Bottom conversion | 0.5384 | 0.6237 | 0.4233 | 0.3933 | 0.4358 | 0.3296 |

Those skilled in the art will recognize that the above embodiments are merely illustrative, and that variations on the above description may be made while staying within the scope of the present invention.

What is claimed is:

1. A process of converting oxygenate to olefin product in a riser, comprising the steps of:
    a) contacting olefin forming catalyst flowing through a contacting conduit in a gaseous medium in an upstream region of the riser with individual jets of gaseous oxygenate introduced into the contacting conduit through a sidewall of the contacting conduit and at an angle between 30° and 75° inclined from the flow of the olefin forming catalyst to initiate conversion of the oxygenate to olefin product, decreasing the angle to increase the rate of conversion in the bottom zone of oxygenate to olefin and creating an interstitial space between the jets that is occupied by solid catalyst particles;
    b) mixing together the individual jets of oxygenate downstream of contact at a location within the contacting conduit;
    c) expanding the individual jets of oxygenate as the oxygenate and catalyst flow through the contacting conduit; and
    d) flowing the oxygenate and catalyst from the contacting conduit to a connecting conduit having a cross sectional area less than that of the contacting conduit to continue conversion of the oxygenate to olefin product.

2. The process of claim 1, wherein the individual jets of oxygenate are injected into the contacting conduit at a velocity of from 20 m/sec to 40 m/sec.

3. The process of claim 1, wherein the areas of interstitial space are upstream of the location of where mixing of the individual jets occurs.

4. The process of claim 1, wherein the olefin forming catalyst is flowed through the connecting conduit at a concentration that is less than that of the olefin forming catalyst flowing within the contacting conduit.

5. The process of claim 1, wherein the olefin forming catalyst is flowed through the contacting conduit at a concentration of between about 15 vol % solids to about 65 vol % solids.

6. The process of claim 1, wherein the olefin forming catalyst is flowed through the connecting conduit at a concentration of between about 3 vol % solids to about 15 vol % solids.

7. The process of claim 1, wherein the olefin forming catalyst is flowed through the connecting conduit at a concentration of between about 1 vol % solids to about 5 vol % solids.

8. The process of claim 1, further comprising a step of separating olefin product from the olefin forming catalyst.

9. The process of claim 8, further comprising a step of contacting at least one olefin in the separated olefin product with an olefin forming catalyst to form polyolefin.

10. The process of claim 1, wherein less than 100% of the oxygenate in the contacting conduit is converted to olefin product.

11. The process of claim 1, wherein less than 100% of the oxygenate in the connecting conduit is converted to olefin product.

12. A process of converting oxygenate to olefin product in a riser, comprising the steps of:
   a) contacting olefin forming catalyst flowing through a contacting conduit in a gaseous medium in an upstream region of the riser with individual jets of gaseous oxygenate introduced into the contacting conduit through a sidewall of the contacting conduit and at an angle between 30° and 60° inclined from the flow of the olefin forming catalyst to form a non-homogeneous contact zone within the contacting conduit in which the individual jets of gaseous oxygenate are surrounded by a fluidized bed of catalyst particles, decreasing the angle to increase the rate of conversion in the bottom zone of oxygenate to olefin and creating an interstitial space between the jets that is occupied by solid catalyst particles;
   b) flowing the olefin forming catalyst and oxygenate into a unified flow contact zone within the contacting conduit; and
   c) flowing the olefin forming catalyst and oxygenate from the unified flow contact zone through a connecting conduit having a cross sectional area less than that of the contacting conduit to continue conversion of the oxygenate to olefin product.

13. A process of converting oxygenate to olefin product, comprising the steps of:
   a) flowing an olefin forming catalyst through an initial conduit of a riser in a gaseous medium comprising an upstream initial conduit, a downstream extended conduit, and an expanded contacting conduit located between the extended conduit and the initial conduit;
   b) flowing the olefin forming catalyst from the initial conduit through the expanded contacting conduit having a non-homogeneous contact zone and a unified flow contact zone, the expanded contacting conduit having a cross-sectional area greater than that of the initial conduit;
   c) injecting individual jets of gaseous oxygenate into the non-homogeneous contact zone and contacting the olefin forming catalyst with the individual jets of gaseous oxygenate in the non-homogeneous contact zone of the expanded contacting conduit, wherein the gaseous oxygenate is introduced into the contacting conduit through a sidewall of the contacting conduit at an angle between 30° and 60° inclined from the flow of the olefin forming catalyst, decreasing the angle to increase the rate of conversion in the bottom zone of oxygenate to olefin and creating an interstitial space between the jets that is occupied by solid catalyst particles;
   d) flowing the olefin forming catalyst and oxygenate from the non-homogeneous contact zone to the unified flow contact zone; and
   e) flowing the olefin forming catalyst and oxygenate from the expanded conduit to an extended conduit having a cross sectional area less than that of the expanded conduit to continue conversion of the oxygenate to olefin product.

14. The process of claim 13, wherein the individual jets of oxygenate are injected into the non-homogeneous contact zone at a velocity of from 20 m/sec to 40 m/sec.

15. The process of claim 13, wherein the non-homogeneous contact zone contains areas of interstitial space separating the individual jets of oxygenate.

16. The process of claim 13, wherein the olefin forming catalyst and oxygenate are flowed from the expanded conduit to the extended conduit after coalescence of the individual jets.

17. The process of claim 13, wherein the olefin forming catalyst is flowed through the expanded conduit at a concentration that is less than that of the olefin forming catalyst flowing through the initial conduit.

18. The process of claim 13, wherein the olefin forming catalyst is flowed through the initial conduit at a concentration of between about 15 vol % solids to about 65 vol % solids.

19. The process of claim 13, wherein the olefin forming catalyst is flowed through the extended conduit at a concentration that is less than that of the catalyst flowing through the expanded conduit.

20. The process of claim 13, wherein the olefin forming catalyst is flowed through the expanded conduit at a concentration of between about 3 vol % solids to about 15 vol % solids.

21. The process of claim 13, wherein the olefin forming catalyst is flowed through the extended conduit at a concentration of between about 1 vol % solids to about 5 vol % solids.

22. A process of converting oxygenate to olefin product, comprising the steps of:
   a) flowing an olefin forming catalyst from an initial conduit of a riser in a gaseous medium comprising an upstream initial conduit, a downstream extended conduit, and an expanded conduit located between the extended conduit and the initial conduit, and through a contacting conduit having an expanded cross sectional area;
   b) contacting olefin forming catalyst flowing through the contacting conduit with individual jets of gaseous oxygenate introduced into the contacting conduit through a sidewall of the contacting conduit and at an angle between 30° and 60° inclined from the flow of the olefin forming catalyst to initiate conversion of the oxygenate to olefin product, decreasing the angle to increase the rate of conversion in the bottom zone of oxygenate to olefin and creating an interstitial space between the jets that is occupied by solid catalyst particles;
   c) mixing together the individual jets downstream of contact at a location within the contacting conduit; and
   d) flowing the downstream mixture to a connecting conduit having a cross sectional area less than that of the contacting conduit to continue conversion of the oxygenate to olefin product.

23. The process of claim 22, wherein the individual jets of oxygenate are injected into the contacting conduit at a velocity of from 20 m/sec to 40 m/sec.

24. The process of claim 22, wherein the areas of interstitial space are upstream of the location of where mixing of the individual jets occurs.

25. The process of claim 22, wherein the olefin forming catalyst is flowed through the connecting conduit at a concentration that is less than that of the olefin forming catalyst flowing within the contacting conduit.

26. The process of claim 1, wherein flowing the oxygenate and catalyst from the contacting conduit to a connecting conduit having a cross sectional area less than that of the contacting conduit to continue conversion of the oxygenate to olefin product is at plug flow conditions of a gas superficial velocity of at least 9 m/s.

27. The process of claim 12, wherein flowing the oxygenate and catalyst from the contacting conduit to a connecting conduit having a cross sectional area less than that of the contacting conduit to continue conversion of the oxygenate to olefin product is at plug flow conditions of a gas superficial velocity of at least 9 m/s.

28. The process of claim 13, wherein flowing the oxygenate and catalyst from the contacting conduit to a connecting conduit having a cross sectional area less than that of the contacting conduit to continue conversion of the oxygenate to olefin product is at plug flow conditions of a gas superficial velocity of at least 9 m/s.

29. The process of claim 22, wherein flowing the oxygenate and catalyst from the contacting conduit to a connecting conduit having a cross sectional area less than that of the contacting conduit to continue conversion of the oxygenate to olefin product is at plug flow conditions of a gas superficial velocity of at least 9 m/s.

* * * * *

UNITED STATES PATENT AND TRADEMARK OFFICE
CERTIFICATE OF CORRECTION

| | |
|---|---|
| PATENT NO. | : 7,619,127 B2 |
| APPLICATION NO. | : 10/745771 |
| DATED | : November 17, 2009 |
| INVENTOR(S) | : Jeffrey S. Smith |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 713 days.

Signed and Sealed this

Twenty-sixth Day of October, 2010

David J. Kappos
*Director of the United States Patent and Trademark Office*